Figure 1:
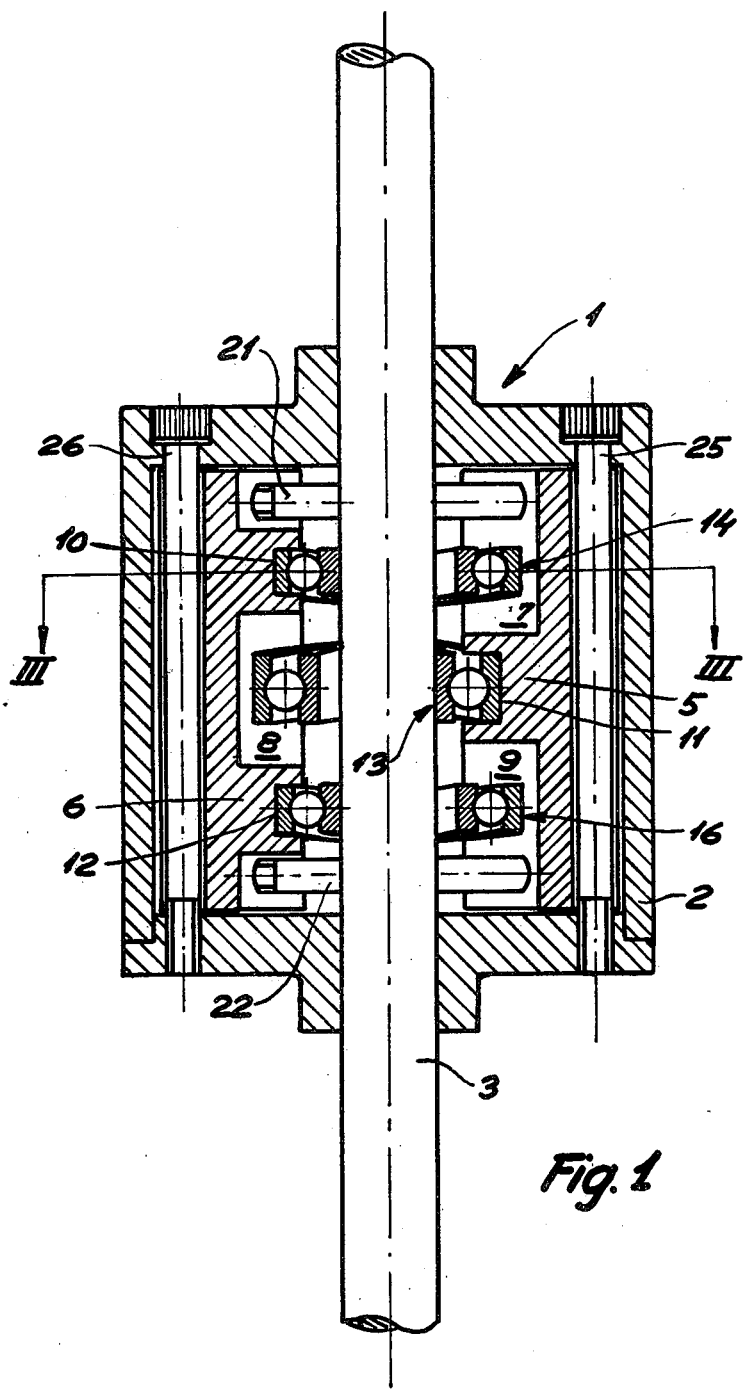

United States Patent [19]

Olrik

[11] 4,008,929
[45] Feb. 22, 1977

[54] FRICTION DRIVE DEVICE

[76] Inventor: Henrik Gerner Olrik, Bakkegaardsvej 413, DK-3050 Humlebaek, Denmark

[22] Filed: Aug. 12, 1975

[21] Appl. No.: 603,917

[30] Foreign Application Priority Data

Aug. 12, 1974 Denmark ............................ 4279/74
July 29, 1975 Denmark ............................ 3431/75

[52] U.S. Cl. .......................... 308/176; 308/189 R; 74/25
[51] Int. Cl.² ....................................... F16C 19/04
[58] Field of Search ............ 308/176, 189 R; 74/25

[56] References Cited

UNITED STATES PATENTS

| 2,940,322 | 6/1960 | Uhing | 74/25 X |
| 3,443,443 | 5/1969 | Spence | 74/25 |
| 3,589,202 | 6/1971 | Stanley | 74/25 |

*Primary Examiner*—Robert R. Song
*Assistant Examiner*—Gene A. Church
*Attorney, Agent, or Firm*—Fleit & Jacobson

[57] ABSTRACT

This invention concerns a self-tightening friction drive device for the conversion of a rotary motion into an axial motion. The device comprises two or more ball bearing jaws retained in angularly spaced position around a shaft, each of the jaws having at least one recess for receiving and supporting a respective ball bearing or roller bearing of larger internal diameter than the external diameter of the shaft extending through the bearings and engaging with the inner rings thereof an inclined angle. Each of the recesses presents in a section perpendicular to the axis of the respective bearing a curve whose radii of curvature are greater than the outer radius of the bearing. In consequence of the inclined position of the bearings relative to the shaft, the bearings will be wedged between the shaft and the bottom of the recesses in response to an axial load on the shaft and will exert an increased pressure against the shaft in response to an increased axial load on the shaft, the pressure being greater when the effective wedge angle is small. The invention further comprises control means adapted to pivot a jaw about a line parallel to the shaft and not merging with the axis of curvature of the supporting recesses, whereby the wedge angle can be controlled in addition to the effect of the actual shape of the recesses.

19 Claims, 11 Drawing Figures

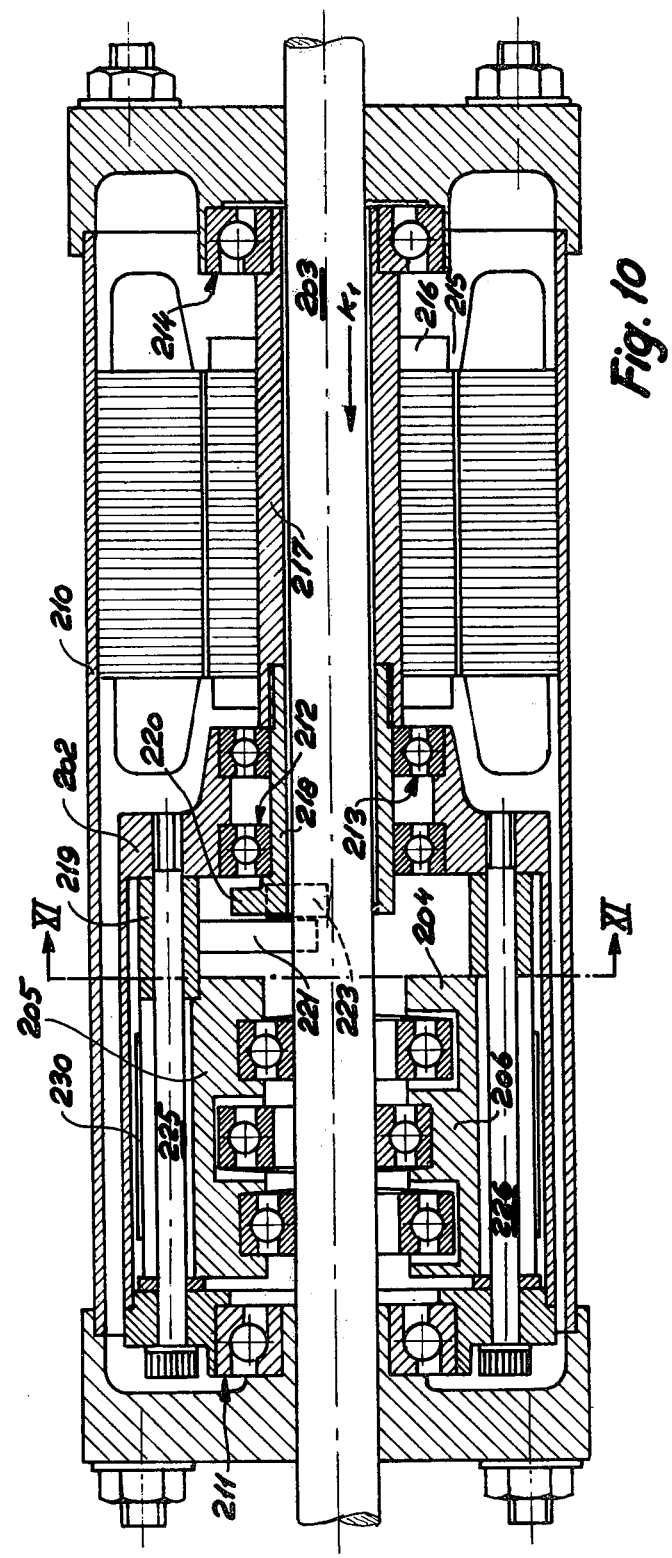

FRICTION DRIVE DEVICE

This invention relates to a friction drive device for converting a rotary motion into an axial motion comprising drive means and, associated with the rotating member thereof, a friction unit containing ball bearings of larger internal diameter than the external diameter of a shaft extending through the motor and the ball bearings and abutting on the inner rings of the bearings at an inclined angle, the friction unit containing further a retaining member in which is provided ball bearing jaws rotating with the retaining member relatively to the shaft and having recesses adapted to support the outer ring of at least one ball bearing and inclined so that the respective bearings abut on the shaft along generating lines for the shaft and on rotation of the jaws roll on the shaft along helical lines of identical pitch and direction.

Thus the conversion of the rotary motion into axial motion is obtained by the inclined position of the ball bearings relative to the shaft which causes the inner rings of the ball bearings to move along a helical line over the surface of the shaft in response to the rotation of the outer rings relative to the shaft about the shaft axis. An intentional friction between the inner rings of the ball bearings and the shaft causes relative axial displacement between the ball bearings and the shaft.

A device of this type is known from Danish Patent application No. 6226/73 which defines a self-tightening friction drive device which in response to increasing relative axial displacement of the ball bearing jaws produces an increasing contact pressure between the jaws, the ball bearings and the shaft. The contact pressure increases evenly and the inner rings slide on the shaft until the jaws have assumed their position of equilibrium. The sliding can be obviated, however, by means of special measures.

One object of the present invention is to provide a self-tightening friction drive device of the said type in which the contact pressure increases instantaneously when a load is applied to the shaft without the bearings sliding thereon.

This object has been accomplished by a device in which two or more ball bearing jaws are retained and angularly spaced apart around the shaft and interconnected by means adapted to receive or counteract the radial pressure of the shaft against the bearings and where the supporting recesses in a section perpendicular to the axis of an associated bearing presents a curve whose radii of curvature are greater than the outer radius of the ball bearing.

Thus the inner and outer rings of the inclined ball bearings are urged into a wedge defined by the shaft and the recesses supporting the ball bearing jaws in response to the axial pressure of the shaft against the ball bearings, and the radial contact pressure will thus increase with decreasing wedge angle, i.e. with increasing radius of curvature of the recesses.

Where the means for receiving the radial pressure of the shaft against the bearings are bolts and mounted so that the jaws are immovable in relation to each other it is possible to obtain a predetermined initial contact pressure between the jaws, the ball bearings and the shaft.

The jaws may be retained against relative axial displacement and the means for receiving the radial pressure of the shaft against the bearings may be a wire wound around the jaws so that the jaws are rotatable about axes parallel to the shaft axis, whereby the said contact pressure will be greater than in the above mentioned embodiment when the device is operating.

A very expedient combination of the features of the instant invention and the tightening means taught by Danish Patent application No. 6226/73 may be obtained if the jaws are axially movable in relation to each other and the means for receiving the radial pressure of the shaft against the bearings is a wire wound around the jaws.

In a very expedient embodiment of the friction drive device according to the invention there are two ball bearing jaws spaced apart by an angular distance of 180°.

Two ball bearings may be supported in one of the said jaws while one ball bearing positioned between the two bearings may be supported in the second jaw. This will prevent deflection of the shaft as a result of the radial forces produced by the ball bearings.

In expedient embodiments of the recesses for supporting the outer rings of the ball bearings the said curve may be a circular arc, or it may be elliptical, or it may be a straight line.

To obviate excessive wear to the device the axial pressure should be only slightly greater than the force necessary for producing a frictional force between the inner rings and the shaft so that these members will not slide relatively to each other, and to avoid damage by heavy overloading the radial pressure must not be able to exceed the permissible dynamic load of the ball bearings. The desired control of the radial pressure in response to the load of the device could be obtained where the recesses for supporting the ball bearings in a section in the plane of the corresponding ball bearing presents a curve of variable radii of curvature, but the manufacture of such ball bearing jaws would be complex and there is therefore need for a device in which the radial pressure can be controlled as mentioned above also where the recesses are for instance circular.

Another object of the invention is to provide a friction drive device that has means for controlling the radial contact pressure produced by means of the said wedge action so that the device will be exposed to a minimum of wear and is secured against damage by overloading.

This object has been accomplished by providing control means cooperating with at least one ball bearing jaw and adapted in response to loads transmitted through the control means to rotate the said ball bearing jaw about a line parallel to the shaft of the device and not merging with the axes of curvature of the supporting recesses.

The advantage of this construction is that the contact pressure is not determined solely by the innate tendency of the ball bearings during operation to wedge in between the shaft and the bottom of the recesses because the wedge angle by means of the aforesaid measures is controlled in response to the load on the device.

An embodiment of the invention where the wedge angle is dependent on the axial load on the shaft comprises a pair of axially toothed control cylinders with merging axes parallel to the shaft of the device and located between at least one end of at least one ball bearing jaw and the retaining member, one of said control cylinders being retained against rotation relative to the associated ball bearing jaw, the other control cylinder being retained against rotation relative to the retaining member and the toothings facing each other in pairs in axial direction for rotation of the ball bearing jaws in response to axial displacement of the ball bearing jaws.

The maximum length of the axial travel of the control cylinders is obtained where the non-cooperating tooth flanks of the control cylinders are substantially parallel to the axes.

The manufacture of the control cylinders will be greatly facilitated where the tooth flank curves of cooperating tooth flanks form a fixed angle with the generating line of the control cylinders, and where each pair of cooperating tooth flanks has tooth flank curves of different curvature there will be non-linear dependence between the wedge angle and the axial load on the shaft.

In a very expedient construction of the device according to the invention the control cylinders for each ball bearing jaw are mounted concentrically about a staybolt secured in the retaining member and serving as carrier member for the said ball bearing jaw while the ball bearing jaws and the retaining member are provided with radial grooves for receiving a complementary projection on each control cylinder facing away from the toothing.

In another embodiment where the wedging action is controlled according to the torque transmitted to the ball bearings the control means include a motordriven curved disc acting as carrier member and adapted for cooperation with rigid carrier means on at least one ball bearing jaw so that the ball bearing jaw is rotated in response to the transmitted torque about the said line parallel to the shaft of the device.

In this embodiment it will also be expedient that the curved disc is associated with an end of a hollow shaft extending through that end of a freely rotating retaining member which faces the driving motor, while two carrier arms are rigidly connected to a sleeve and extending from the sleeve into engagement with opposed sides of the curved disc, said sleeve being mounted concentrically on a staybolt in the retaining member and in engagement with a ball bearing jaw. The said carrier arms abut on the curved disc via steel rollers and the sleeve at the end facing the ball bearing jaw has a projection adapted to be received in a radial slot in the ball bearing jaw.

Figure 2:
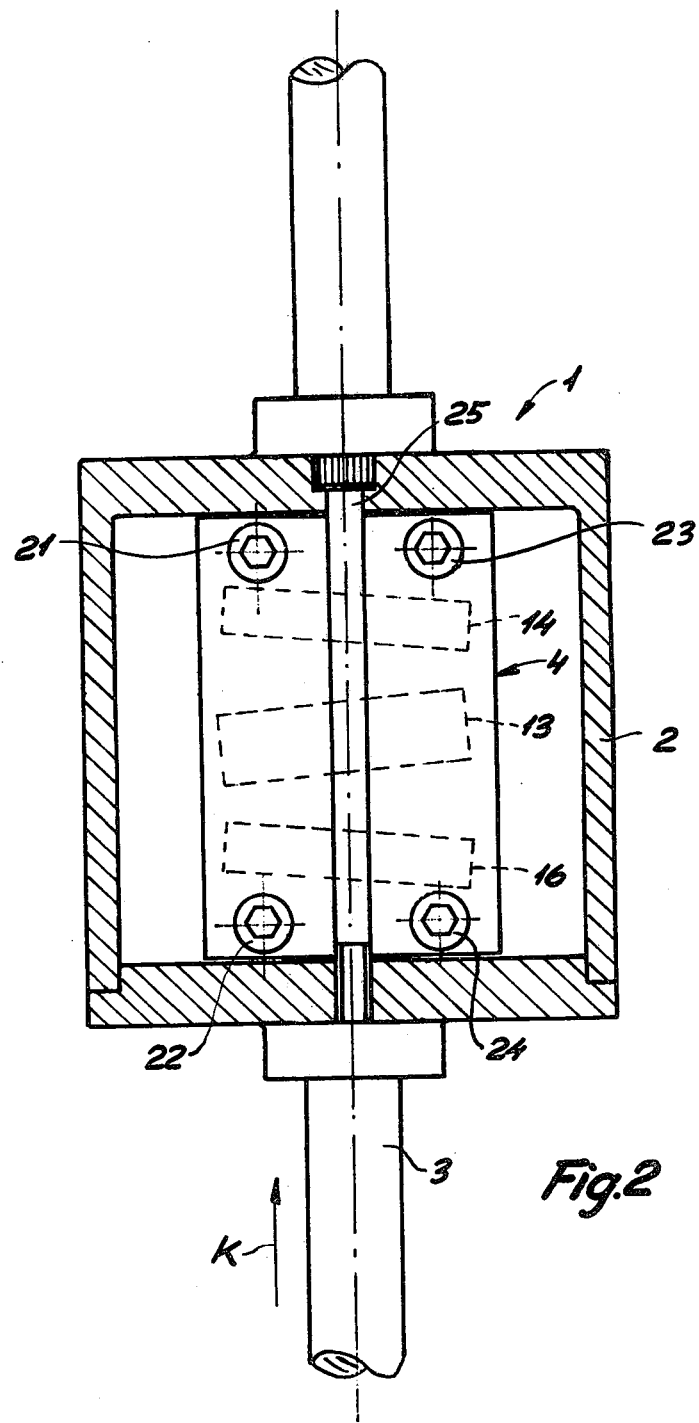
Figure 3:
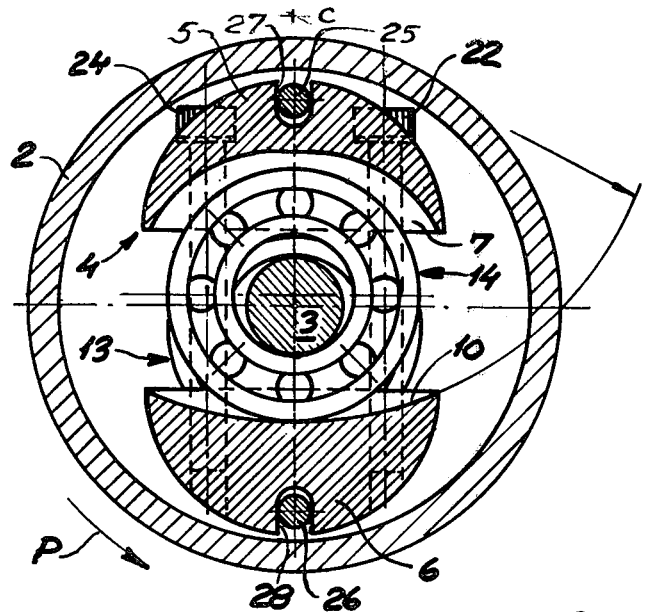
Figure 4:
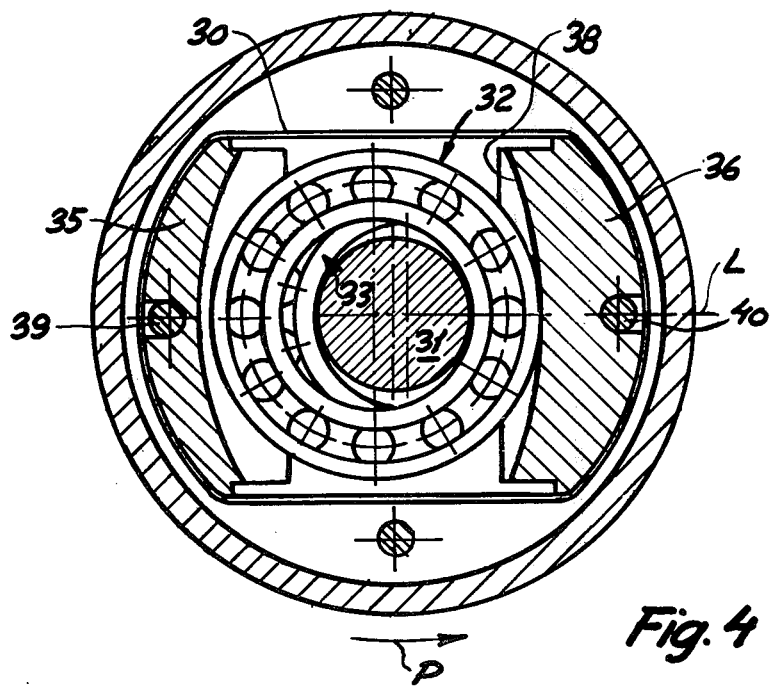
Figure 5:
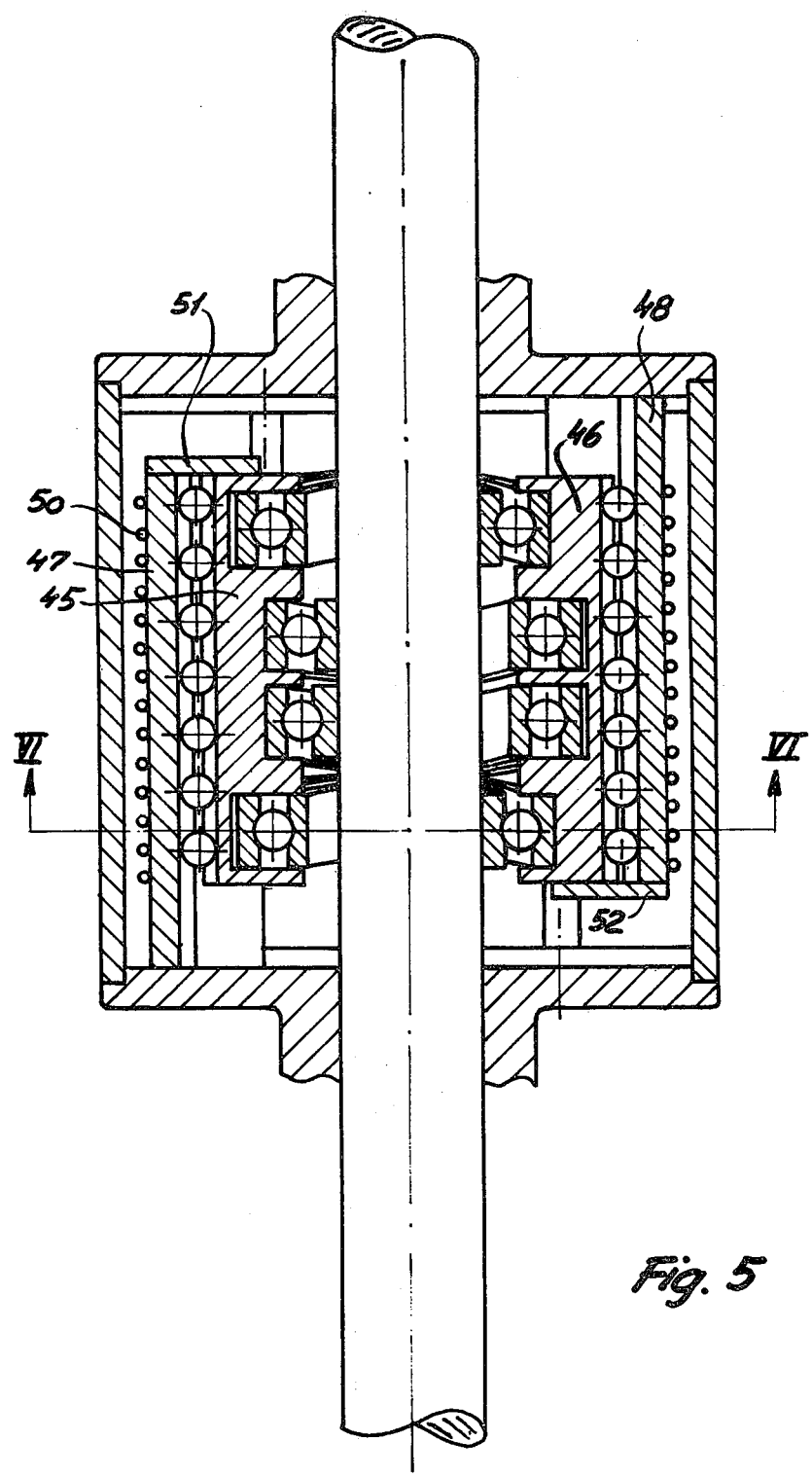
Figure 6:
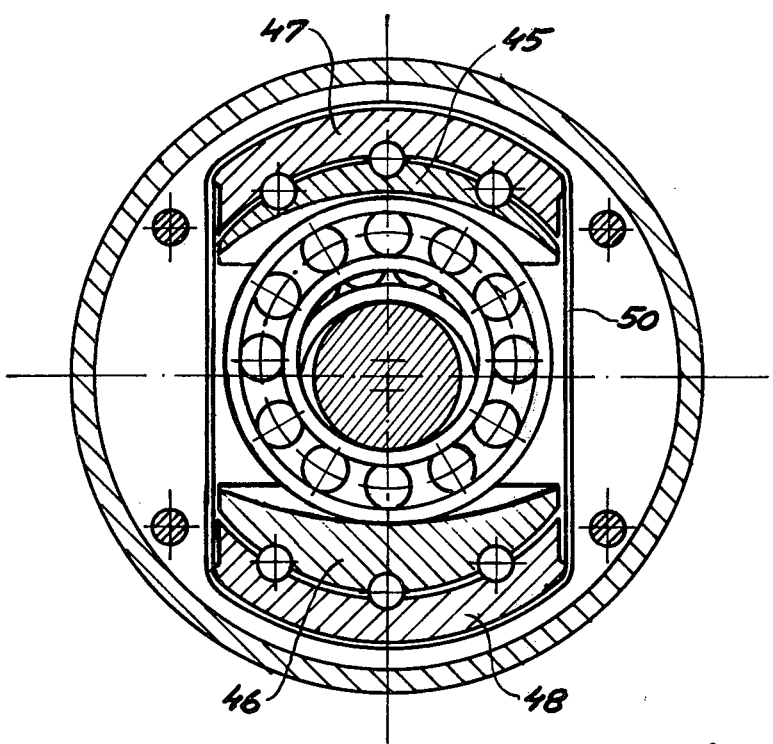
Figure 7:
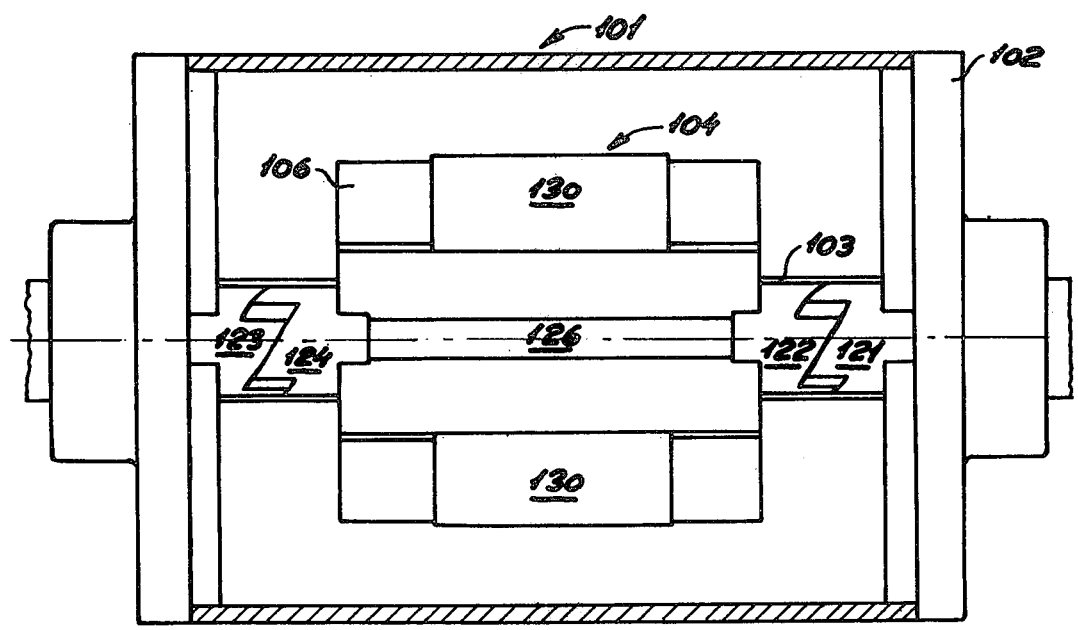
Figure 8:
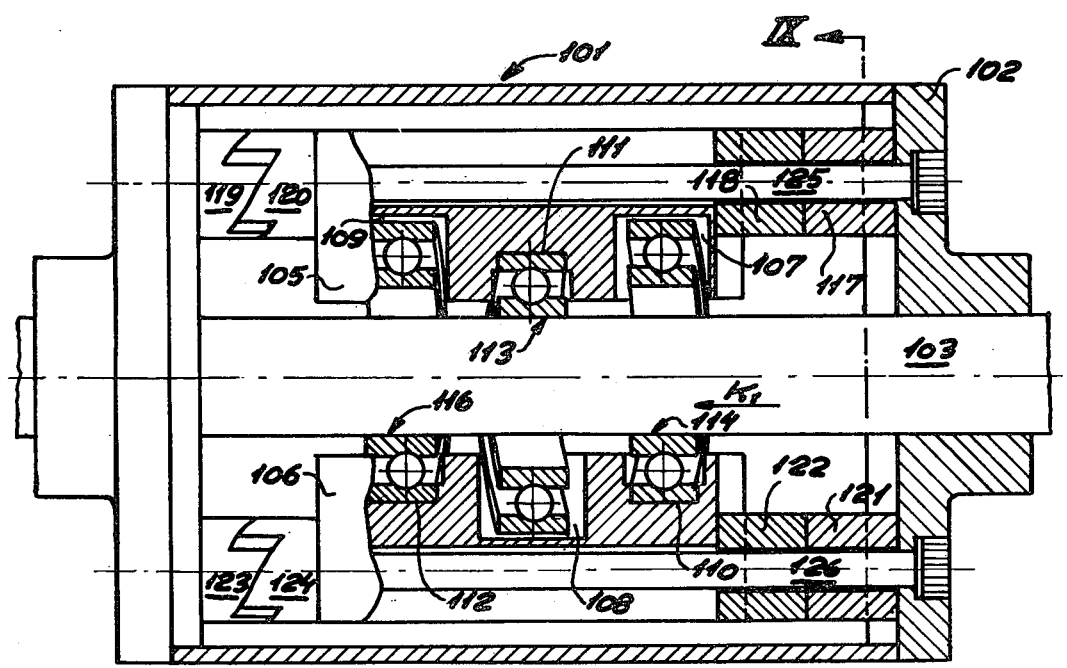
Figure 11:
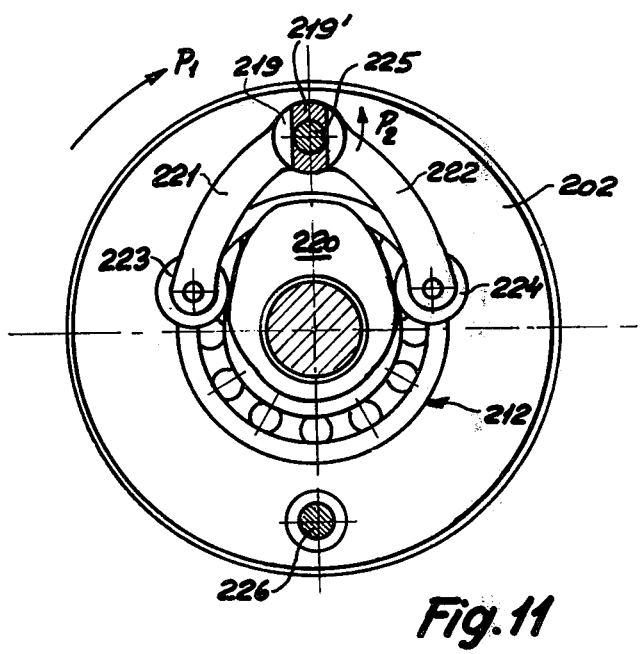

The invention will be explained in greater detail by the following description of some embodiments and with reference to the drawings, in which FIG. 1 presents a section through an embodiment of the frictional drive device according to the invention, FIG. 2 shows the device of FIG. 1 viewed from above, FIG. 3 is a section through the device of FIG. 1 along the line III—III, FIG. 4 presents a section like that of FIG. 3 through a second embodiment of the invention, FIG. 5 presents a section through a third embodiment of the friction drive device according to the invention, FIG. 6 is a section through the device of FIG. 5 along the line VI—VI, FIG. 7 shows a fourth embodiment of the friction drive device according to the invention viewed from below, FIG. 8 is a vertical section through the embodiment of FIG. 7, FIG. 9 a section along the line IX—IX of FIG. 8, FIG. 10 shows a fifth embodiment of the friction drive device according to the invention, and FIG. 11 is a section along the line XI—XI in FIG. 10.

The embodiment of the invention illustrated in FIGS. 1, 2 and 3 has a housing 2 in which a friction unit 4 is mounted around a shaft 3. The friction unit comprises two ball bearing jaws 5 and 6 with recesses for supporting or receiving the ball bearings of the unit. The jaw 5 has recesses 11 for supporting the outer ring of a ball bearing 13 and recesses 7, 9 for receving ball bearings 14 and 16 respectively. The jaw 6 has a recess 8 for receiving the bearing 13 and recesses 10, 12 for supporting the outer rings of the bearings 14 and 16 respectively. The recesses are inclined with respect to the shaft 3 and the width of the supporting recesses corresponds to the width of the outer ring of the associated ball bearing so that the bearings are retained in the inclined position indicated in FIGS. 1 and 2. The width of the receiving recesses is in actual practice smaller than indicated in FIG. 1 with the result that between the recesses and the bearing there is a clearance in the axial direction of the bearing of a few tenths of a millimeter. The bearings are retained in engagement with the shaft by a predetermined pressure by means of bolts 21, 22, 23, 24 which retain the jaws 5, 6 in rigid relationship. The inner rings of the bearings may be elliptically cut in conventional manner and will thus abut on the shaft 3 along substantially diametrically opposed generating lines of the shaft.

The drive device 1 is caused to rotate about the shaft 3, which is retained against rotary motion. Rotation may be provided for instance by means of an electromotor with a hollow shaft for receiving the shaft 3, as defined in greater detail in the specification of Danish Patent application No. 6226/73. By means of staybolts 25, 26 secured in the housing 2 and extending through axial millings, 27 and 28 respectively, in the jaws the jaws are caused to follow in the rotary motion.

The operation will be described here with reference to FIG. 3 and it is assumed that the jaws are caused to rotate in the direction of the arrow P. During rotation the inner rings of the ball bearings will roll on the shaft along such helical lines that the shaft 3 is moved downwards in FIG. 1, the shaft is subjected to the force K indicated in FIG. 2 it will be seen from that figure that the bearings 14, 16 will be subject to a left-directed force, whle the bearing 13 will be subject to a right-directed force, said forces being conditioned by the inclined position of the bearings relative to the shaft. Applied to FIG. 3 this means that the bearing 14 rolls towards right in the recess 10 so that the contact line between the outer ring and the bottom of the recess moves towards right, while the contact line between the inner ring and the shaft moves towards left.

The above described bearing motion causes the contact pressure between the ball bearing and respectively the shaft and the ball bearing jaw to increase with the increase of the torque translated to the axial load, the radial force produced by the bearings 14, 16 being balanced by the equal force produced by the bearing 13.

The result is a dynamical self-tightening device, that is to say the said contact forces and the consequent friction between the shaft and the inner rings of the bearings increase with increasing torque and axial load. When the drive device does not rotate an axial force applied to the shaft 3 will cause a certain static self-tightening, in that for instance the bearing 14 as a result of the friction and its inclined position relative to the shaft will roll slightly to the right (FIG. 3) when the force K shown in FIG. 2 is applied to the shaft. The self-tightening will have a greater effect the greater the pitch of the helical lines along which the bearings roll on the shaft 3.

This invention has attained not only a dynamic self-tightening but also an automatic correct centering of the bearings. The shape of the supporting recesses could be used directly in the construction of a self-tightening device with adjustable pitch, i.e. adjustable rotary/axial transformation ratio. When using two bearings 14, 16, each on one side of a more sturdy bearing 13 the points of application of forces perpendicular to the shaft 3 can be brought so close together that the shaft will not deflect.

In FIG. 3, C is the centre of curvature of the recess 10. The bottom of the recess according to the invention may have other shapes, for instance rectilinear or a shape that will cause an actual magnitude. As a result of the axial pressure of the shaft against the inclined ball bearings the inner and outer rings of the bearings are urged into a wedge defined by the shaft and the recesses of the ball bearing jaws, and the radial contact pressure will therefore increase with decreasing wedge angle, viz. with increasing radius of curvature of the recesses. The recesses may even to a certain degree be convex in that the jaws 5, 6 rotate about the axis of the shaft 3, which in FIG. 3 is lower than the axis of the bearing 14, and the bearing is urged towards right when the jaws rotate in the direction of the arrow P.

The bolts 21, 22, 23, 24 shown in FIG. 2 may be replaced by a resilient wire 30 (see FIG. 4) which is wound around the jaws in the manner described in Danish Patent application No. 6226/73.

As described in connection with FIG. 3 the reaction from the shaft 31 will cause the ball bearing 32 to move towards right when the jaws 35, 36 are rotated in the direction of the arrow P. The contact line between the outer ring and the bottom of the recess will rise over the line L (FIG. 4) and the previously mentioned radial pressure from the ball bearings will urge the jaws 36 into clockwise rotation about the staybolt 40 and as a result of the displacement of the bearing 33 downward the jaw 35 will also be urged into clockwise rotation about the staybolt 39. Owing to the resiliency of the wire 30 the jaws will thus rotate in a manner by which the aforesaid wedge angle is reduced and the result will be a higher contact force than in the previously described embodiment, provided that the radii of curvature of the recesses 10 and 38 are identical.

The specific advantage of this embodiment is that the radii of curvature of the recesses may be smaller than previously with the attainment of the same contact force, whereby the Hertz pressure at the abutment of the outer ring against the recess will be smaller.

If a greater contact force is desired, especially when the device is not rotating, it can be attained by the recesses 7, 8 and 9 having the widths shown in FIG. 1 and at the same time providing a greater clearance than that indicated between the jaw 5 and one end wall of the housing 2 and between the jaw 6 and the opposed end wall of the housing. One of the end walls of the housing acts as end stop for the jaw 6 and the opposed end wall acts as end stop for the jaw 5 to provide relative axial displacement of the jaws when the shaft 3 is subject to an axial force. In consequence of the relative axial displacement the resilient wire 30 in FIG. 4 will clamp the jaws 5, 6 against each other as described in greater detail in Danish Patent application No. 6226/73. From that patent it is known that the bearings slide a certain length on the shaft before the increased contact force is produced, but as a result of the combination of this effect with the shape of the supporting recesses according to the present invention a certain fraction of the total contact force, viz. the part deriving from the dynamic self-tightening, sets in instantaneously with the application of the force, whereas the last part of the contact force, viz. the part deriving from the relative axial displacement, appears gradually.

If it is desired to obviate the said slide of the bearings on the shaft the invention may be applied in combination with the embodiments taught by Danish Patent Of Addition application No. 940/74.

FIGS. 5 and 6 illustrate such a combination in which the ball bearing jaws 45, 46 have recesses according to the invention and which is further provided with respective roller jaws 47, 48 around which the resilient wire 50 is wound. On the application of an axial force to the shaft the first ball bearing jaw 45 or 46 rolls on the associated roller jaw 47 or 48. There is no axial clearance between the bearings and the recesses in the ball bearing jaws and the second ball bearing jaw will therefore follow in the axial movement of the first ball bearing jaw and via an end flange 51 or 52 displace the associated roller jaw relatively to the second roller jaw, whereby the resilient wire 50 will be tightened.

In this way all the previously mentioned advantages have been achieved without the inner rings of the bearings sliding on the shaft, which is thus less exposed to wear.

The axial pressure, as already mentioned, should be but slightly greater than the force necessary for producing a frictional force between the inner rings and the shaft to prevent sliding between these members, and to avoid damage by heavy overloading, the radial pressure should not be allowed to exceed the permissible dynamic load of the ball bearings. The required control of the radial pressure in response to the load of the device will, as also mentioned, be obtained if the recesses adapted to support the ball bearings in a section in the plane of the associated ball bearing present a curve with variable radii of curvature. The manufacture of such ball bearing jaws would be complex and there is therefore need for a device in which the radial pressure can be controlled as mentioned above, also where the recesses are for example circular. Two such embodiments will be described below.

Figure 9:
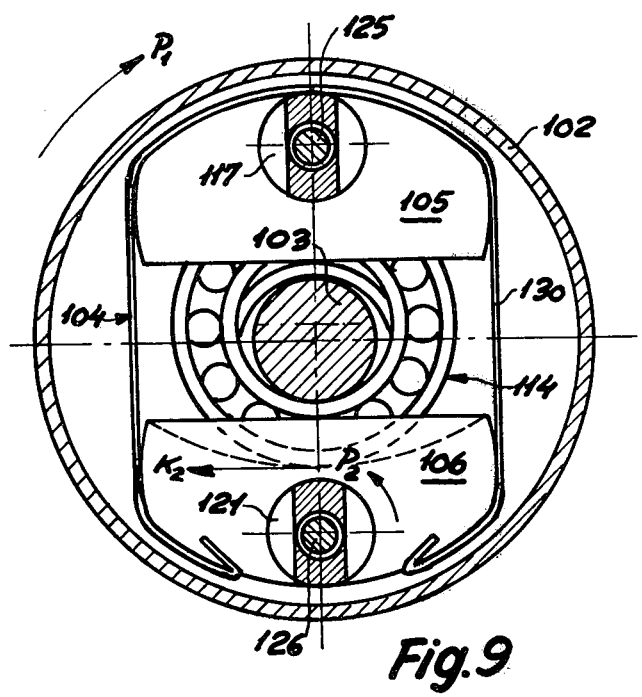

The friction unit 104 in FIGS. 7, 8, and 9 comprises two ball bearing jaws 105, 106 for supporting ball bearings 113, 114, 116 which are inclined relative to a shaft 103 extending through the device. The ball bearing jaw 105 has a recess 111 for supporting the outer ring of the ball bearing 113, the bottom of the recess having a larger radius of curvature than the outer radius of the bearing. This jaw is further provided with recesses 107, 109 for receiving the ball bearings 114, 116 which are supported in recesses 110, 112 in the ball bearing jaw 106, said recesses having a larger radius of curvature than the outer radius of the associated bearings. The jaw 106 also has a recess 108 for receiving the ball bearing 113. The supporting recesses 111, 110, 112 and the associated ball bearings 113, 114, 116 are so inclined relative to the shaft 103 that the ball bearings on rotation of the retaining member 102 roll on the shaft 103 along helical lines with identical pitch and the shaft 103 is thus urged to perform an axial movement when the device is rotated and retained against axial motion. For interconnection of the ball bearing jaws 105, 106 is provided a resilient band 130 enclosing the jaws and secured in axial grooves in the ball bearing jaw 106. By means of the resilient band 130 the ball bearing jaws 105, 196 may be subjected to a certain pre-tension against the shaft 103 to produce the friction between the shaft 103 and the inner rings of the ball bearings 113, 114, 116 necessary for the movement of the shaft 103.

If the device is rotated for instance in the direction indicated by the arrow P1 in FIG. 9 the shaft 103 in FIG. 8 will be urged towards right. A force applied to the device will produce a reactive force K1 that will cause the bearings to roll sideways as a result of their inclined position in relation to the shaft. As shown in FIG. 9 the ball bearing 114 will be subjected to a force K2 which is directed towards left so that the ball bearing is wedged between the shaft 103 and the associated recess in the ball bearing jaw 106, the contact line for the abutment of the outer ring against the bottom of the recess being displaced towards left, while the contact line for the abutment of the inner rings against the shaft being displaced towards right. The other ball bearings are similarly wedged between the shaft 103 and the bottom of the associated supporting recess. As already explained, this ball bearing motion will cause a certain torque of the ball bearing jaws 105, 105 about the staybolts 125 and 126 respectively in the direction indicated by the arrow P2 in FIG. 9.

The invention also includes means for producing the said torque independently of the sideways ball bearing motion. These means comprise toothed guide cylinders 117, 119, 121, 123, 118, 120, 122, 124 mounted in pairs between the ends of each of the ball bearing jaws 105, 106 and the end flanges of the retaining member 102 and concentrically about the associated staybolts 125, 126. The guide cylinders have opposite pairs of cooperating toothings with axiallly parallel tooth flanks and tooth flanks inclined in relation thereto. Opposite the toothing each guide cylinder has a projection for cooperation with radial slots in the end flanges of the retaining member 102 and in the end faces of the ball bearing jaws 105, 106 so that a relative axial displacement between the friction unit 104 and the retaining member 102 causes the ball bearing jaws 105, 106 to rotate around the associated staybolts 125, 126 in response to the pitch of the inclined tooth flanks. The pitch direction in this embodiment is selected so that the ball bearing jaws 105, 106 are rotated in the direction indicated by the arrow P2 in FIG. 9 when the shaft 103 is subjected to the force K1. Thereby the said wedge angle will be less and the radial contact pressure greater than that obtainable in the previously described embodiments provided that the force K1 is the same.

It is important that the guide cylinders remain engaged in pairs so as to limit the axial displacement of the friction unit 104 relative to the retaining member 102. On account of the axially parallel tooth flanks the maximum displacement is obtained, besides which the tooth flanks serve as end stops for the ball bearing jaws and thus put an upper limit to the lateral movement of the ball bearings and consequently an upper limit to the radial pressure of the bearings on the shaft 103 to protect it against overloading.

The inclined tooth flanks might also have a pitch opposite to that indicated in FIGS. 7 and 8 so that the wedge effect is counteracted. If a non-linear connection between the rotation of the ball bearing jaws 10, 16 about the staybolts 125, 126 in response to the axial load on the shaft 103 is wanted, the non-axially parallel tooth flanks of one of a pair of guide cylinders could present tooth flank curves of non-uniform curvature for cooperation with a cam on the second of the pair of guide cylinders. Thus it is possible by means of the described guide cylinders to obtain an arbitrary regulation of the wedge action as a result of the bottom of the supporting recesses having a greater radius of curvature than the outer radius of the associated ball bearing. As a consequence of this regulating effect it is not necessary for the jaws to be axially displaceable with respect to each other to increase the radial contact pressure. The piano wire suggested by Danish Patent application No. 6226/73 to be wound around the jaws can therefore, as shown in the figures, be replaced by the resilient band 130 which is adapted to receive the pressure of the ball bearings on the shaft and permit the jaws to rotate around the associated staybolts without possibility of mutual axial movement. This involves the advantage that there will be no transition in the gear ratio when the direction of rotation of the retaining member and thereby the direction of movement of the shaft is changed. This is of specific importance where the drive device is used as feeding device in machine tools.

In the embodiment described with reference to FIGS. 7, 8 and 9 it was presupposed that the resilient band 130 caused a certain pre-tension of the ball bearing jaws against the shaft to ensure that they could be rotated to regulate the wedge action. The shaft, therefore, is not free even if the device has been stopped.

In certain cases it may be convenient for the shaft to be freely pushed through the device when it is stopped, and FIGS. 10 and 11 illustrate such an embodiment of the friction drive device according to the invention. This embodiment is adapted to utilize the torque transmitted to the ball bearings for rotating the ball bearing jaws as described above. The retaining member 202 is therefore supported to be freely rotatable in a motor housing 210 by means of ball bearings 211–214. The torque from the rotor 216 of a motor 215 is transmitted through a hollow motor shaft 217 and a hollow shaft 218 according to the invention to the ball bearings in the jaws 205, 206 in the manner described below.

The friction unit 204 is designed like the friction unit 104 in FIGS. 7–9, but instead of being adapted to receive the said guide cylinders it is provided with a radial slot in the end of the ball bearing jaw 205 facing the motor for cooperation with a projection 219′ on a sleeve mounted concentrically around the staybolt 225. To the sleeve 219 are secured two arms 221, 222 (FIG. 11) extending on either side of a curved disc 220 rigidly connected to the hollow shaft 218. Each arm is provided on the end with rolls 223, 224 for cooperation with the profiled edge of the curved disc 220.

In the following description of the operation it is assumed that the rotor 216 and thereby the disc 220 rotate in the direction indicated by the arrow P1 in FIG. 11. The ball bearings in the jaws 205, 206 are so inclined that the shaft 203 in FIG. 10 will be subjected to a force directed towards the right so that an applied force will result in a reactive force K1. When the axial load increases, an increasing torque shall be transmitted to the ball bearing jaw 205 and through the resilient band 230 to the ball bearing jaw 206, which causes the arm 222 to rotate the sleeve 219 in the direction indicated by the arrow P2 in FIG. 11 as a result of the cooperation between the roll 224 and the profiled edge of the disc 220. As a result of the engagement between the projection 219' and the ball bearing jaw 205 this jaw too will be rotated in the direction of the arrow P2 and through the resilient band 230 the ball bearing jaw 206 will also be rotated in that direction. Thus the same effect has been attained as in the embodiment illustrated in FIGS. 7-9, but in a manner such that the effect is not dependent on a pretension of the ball bearing jaws 205, 206 against the shaft 203 produced by means of the resilient band 230, and the shaft is therefore freely movable through the device when no torque is transmitted, that is when the device does not rotate. The embodiment shown in FIGS. 10 and 11 has the further advantage over that of FIGS. 7-9 that it is very easy to provide non-linear connection between the rotation of the jaws about the associated staybolts (225, 226) and the transmitted torque because the profile of the disc 220 can be made in a simple process by copy-milling. The embodiments illustrated in FIGS. 7-11 are particularly expedient as self-tighteners for drive devices with adjustable ball bearing pitch.

What I claim is:

1. A friction drive device for converting a rotary motion into an axial motion comprising drive means and, associated with the rotating member thereof, a friction unit containing ball bearings of larger internal diameter than the external diameter of a shaft and abutting on the inner rings of the bearings at an inclined angle, the friction unit containing further a retaining member in which is provided ball bearing jaws rotating with the retaining member relatively to the shaft and having recesses adapted to support the outer ring of at least one ball bearing and inclined so that the respective bearings abut on the shaft along generating lines and on rotation of the jaws roll on the shaft along helical lines of identical pitch and direction, characterized in that two or more ball bearing jaws (5, 6, 35, 36, 45, 46) are retained and angularly spaced apart around the shaft (3, 31) and interconnected by means (21, 22, 23, 23, 30, 50) adapted to receive the radial pressure of the shaft (3, 31) against the bearings (13, 14, 16, 32, 33), and that the supporting recesses (10, 11, 12, 38) in a section perpendicular to the axis of an associated bearing (14, 13, 16, 32) presents a curve whose radii of curvature are greater than the outer radius of the ball bearing (14, 13, 16, 32).

2. A device according to claim 1, characterized in that the means for receiving the radial pressure of the shaft (3) against the bearings (13, 14, 16) are bolts (21, 22, 23, 24) which are so mounted that the jaws (5, 6) are immovable relative to each other.

3. A device according to claim 1, characterized in that the jaws (35, 36) are retained against relative axial displacement and that the means for receiving the radial pressure of the shaft (31) against the bearings (for instance 32) is a wire (30) wound around the jaws (35, 36).

4. A device according to claim 1, characterized in that the jaws (35, 36) are relatively axially movable and that the means for receiving the radial pressure of the shaft (31) against the bearings (for instance 32) is a wire (30) wound around the jaws (35, 36).

5. A device according to claim 1, characterized in that there are two ball bearing jaws (5, 6, 35, 36, 45, 46) spaced apart by an angular distance of 180°.

6. A device according to claim 5, characterized in that two ball bearings (14, 16) are supported in one jaw (6) and that one ball bearing (13) disposed between the aforesaid two bearings is supported in the other jaw (5).

7. A device according to claim 1, characterized in that the said curve is a circular arc.

8. A device according to claim 1, characterized in that the curve is elliptical.

9. A device according to claim 1, characterized in that the curve is a straight line.

10. A device according to claim 1, characterized by control means cooperating with at least one ball bearing jaw (105, 205) and adapted in response to forces transmitted via the control means to rotate the said ball bearing jaw (105, 205) about a line parallel to the shaft (103, 203) of the device and not merging with the axes of curvature of the supporting recesses (110, 111, 112).

11. A device according to claim 10, characterized by a pair of axially toothed control cylinders (117, 118, 119, 120, 121, 122, 123, 124) with merging axes parallel to the shaft (103) of the device and located between at least one end of at least one ball bearing jaw (105, 106) and the retaining member (102), one of said control cylinders (118, 120, 122, 124) of a pair being retained against rotation relative to the associated ball bearing jaw (105, 106), the other control cylinder (117, 119, 121, 123) of the pair being retained against rotation relative to the retaining member (102) and the toothings facing each other in pairs in axial direction for rotation of the ball bearing jaws (105, 106) in response to axial displacement of the ball bearing jaws (105, 106).

12. A device according to claim 1, characterized in that the non-cooperating tooth flanks of the control cylinders (117, 118, 119, 120, 121, 122, 123, 124) are substantially parallel to the axis of a pair.

13. A device according to claim 11, characterized in that the tooth flank curves of cooperating tooth flanks form a fixed angle with the generating line of the control cylinders (117, 118, 119, 120, 121, 122, 123, 124).

14. A device according to claim 11, characterized in that each pair of cooperating tooth flanks has tooth flank curves of different curvature.

15. A device according to claim 11, characterized in that the control cylinders (117, 118, 119, 120, 121, 122, 123, 124) for each ball bearing jaw (105, 106) are mounted concentrically about a staybolt (125, 126) secured in the retaining member and serving as carrier member for the said ball bearing jaw (105, 106), and that the ball bearing jaws (105, 106) and the retaining member (102) are provided with radial grooves for receiving a complementary projection on each control cylinder (117, 118, 119, 120, 121, 122, 123, 124) facing away from the toothing.

16. A device according to claim 10, characterized that the control means include a motordriven curved disc (220) acting as carrier member and adapted for cooperation with rigid carrier means on at least one ball bearing jaw (205) so that the ball bearing jaw (205) is rotated about the said line parallel to the shaft of the device (204) in response to the transmitted torque.

17. A device according to claim 16, characterized in that the curved disc (220) is rotated via a hollow shaft (218) extending through that end of a freely rotating retaining member (202) which faces the driving motor (215).

18. A device according to claim 16, characterized by two carrier arms (221, 222) rigidly connected to a sleeve (219) and extending from the sleeve into engagement with opposed sides of the curved disc (220), said sleeve (219) being mounted concentrically on a staybolt (225) in the retaining member and in engagement with a ball bearing jaw (205).

19. A device according to claim 18, characterized in that the carrier arms (221, 222) abut on the curved disc (220) via steel rollers (223, 224) and that the sleeve (219) at the end facing the ball bearing jaw (205) has a projection (219′) adapted to be received in a radial slot in the ball bearing jaw (205).

* * * * *